(12) United States Patent
Guevremont

(10) Patent No.: US 7,285,774 B2
(45) Date of Patent: Oct. 23, 2007

(54) FAIMS APPARATUS AND METHOD FOR SEPARATING IONS IN THE GAS PHASE

(75) Inventor: Roger Guevremont, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 146 days.

(21) Appl. No.: 10/529,304

(22) PCT Filed: Sep. 23, 2003

(86) PCT No.: PCT/CA03/01445

§ 371 (c)(1),
(2), (4) Date: Mar. 25, 2005

(87) PCT Pub. No.: WO2004/030129

PCT Pub. Date: Apr. 8, 2004

(65) Prior Publication Data
US 2006/0038121 A1    Feb. 23, 2006

Related U.S. Application Data

(60) Provisional application No. 60/413,162, filed on Sep. 25, 2002.

(51) Int. Cl.
*B01D 59/44* (2006.01)
(52) U.S. Cl. .................. 250/290; 250/292; 250/287; 250/282
(58) Field of Classification Search ........... 250/290
See application file for complete search history.

(56) References Cited

U.S. PATENT DOCUMENTS

| 4,234,791 A | 11/1980 | Enke et al. |
| 5,847,386 A | 12/1998 | Thomson et al. |
| 6,111,250 A | 8/2000 | Thomson et al. |
| 6,124,592 A * | 9/2000 | Spangler .................. 250/287 |
| 6,512,224 B1 | 1/2003 | Miller et al. |
| 6,621,077 B1 | 9/2003 | Guevremont et al. |
| 6,639,213 B2 | 10/2003 | Gillig et al. |
| 6,744,043 B2 | 6/2004 | Loboda |
| 6,822,224 B2 | 11/2004 | Guevremont |
| 7,034,292 B1 * | 4/2006 | Whitehouse et al. ....... 250/289 |
| 2001/0032929 A1 | 10/2001 | Fuhrer et al. |

FOREIGN PATENT DOCUMENTS

WO    WO 99/30350    6/1999

* cited by examiner

*Primary Examiner*—Nikita Wells
*Assistant Examiner*—Phillip A. Johnston
(74) *Attorney, Agent, or Firm*—Freedman & Associates

(57) ABSTRACT

Disclosed is a high field asymmetric waveform ion mobility spectrometer (FAIMS) including a set of spaced-apart parallel rods, the space between the parallel rods having first and second ends and defining an analyzer region. The apparatus includes an electrical controller for electrically coupling to the set of parallel rods, for applying at least an rf-voltage between the parallel rods of the set of parallel rods in a first operating mode and for applying a combination of an asymmetric waveform voltage and a direct current voltage between the parallel rods of the set of parallel rods in a second operating mode.

36 Claims, 12 Drawing Sheets

FAIMS APPARATUS AND METHOD FOR SEPARATING IONS IN THE GAS PHASE

This application claims the benefit of U.S. Provisional Application No. 60/413,162, filed Sep. 25, 2002.

FIELD OF THE INVENTION

The instant invention relates generally to a method and apparatus for separating ions in the gas-phase, more particularly the instant invention relates to a high field asymmetric waveform ion mobility spectrometry (FAIMS) apparatus having multipole electrode geometry and a method therefore.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength. It is to be understood that the strength of the field is actually E/N where E is the field in volts/cm and N is the number density of the bath gas. Clearly, the application of lower voltages is appropriate under conditions of lower gas pressure while higher voltages are required at higher gas pressure, each arriving at the same E/N. The behavior of ions in the FAIMS technology is based on changes in the mobility of the ion under conditions of changing E/N, which is often simplified to "conditions of changing electric field strength."

In general, a device for separating ions according to the FAIMS principle has an analyzer region that is defined by a space between first and second spaced-apart electrodes. By way of example, the first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV.

In FAIMS, the optimum dispersion voltage waveform for obtaining the maximum possible ion detection sensitivity takes the shape of an asymmetric square wave with a zero time-averaged value. In practice this asymmetric square waveform is difficult to produce. Since a tuned circuit cannot provide a square wave, an approximation of a square wave is taken as the first terms of a Fourier series expansion. One possible approach is to use:

$$V(t) = A\sin(\omega t) + B\sin(2\omega t - \Theta) \qquad (1)$$

where V(t) is the asymmetric waveform voltage as a function of time, A is the amplitude of a first sinusoidal wave having frequency ω, B is the amplitude of a second sinusoidal wave having frequency 2ω, and Θ is the phase shift between the first and second sinusoidal waves.

A number of suitable electrode geometries have been described for use with FAIMS. Some examples include electrode geometries that are based on concentric cylinders, parallel flat plates and parallel curved plates. In WO 01/69647, published 20.09.2001, the instant inventor discloses a FAIMS analyzer including four parallel rods arranged as in a conventional linear quadrupole mass spectrometer. A linear quadrupole mass spectrometer employs four parallel spaced hyperbolic surfaces with appropriate voltages to establish a two-dimensional quadrupole field. A popular close approximation to the hyperbolic surfaces uses four parallel spaced round rods. Such mass spectrometers act as a filter, transmitting ions in a selected range of mass-to-charge (m/z) ratios when the ions are injected into one end of the elongated space between the rods.

The quadrupole rods in a linear quadrupole mass spectrometer are used in two ways. If only a radio frequency (rf) sinusoidal waveform is applied to the rods, the rods are said to be operating in rf-only mode. In this mode a wide range of ions of differing mass are transmitted simultaneously. When a vacuum is maintained within the space between the rods, there is a low probability that the ions will collide with a neutral molecule. Alternatively, a bath gas may be present within the space between the rods. Typically, the bath gas pressure is lower than atmospheric pressure, perhaps a few millitorr, which is sufficient to collisionally cool the ions moving through the space between the rods, and to induce collisional dissociation of the ions to form daughter ions or fragment ions. Under these operating conditions, the quadrupole rods define a quadrupole collision cell.

In a second mode, referred to as the mass analyzer mode, a dc voltage is superimposed on the rf sinusoidal waveform voltage that is applied between the rods and the mass range of ions whose trajectories remain stable is significantly reduced. With the appropriate rf and dc voltages, ions within a mass range of one m/z can be stable and all others collide with the walls of the quadrupole rods. Of course, high vacuum conditions are necessary for operation in the mass analyzer mode.

As was mentioned above, a FAIMS mode of operation is also possible by the application of an appropriate combination of asymmetric waveform and dc potentials between the parallel rods. The behavior of ions in the FAIMS technology is based on changes in the mobility of the ion under conditions of changing E/N. The conventional high pressure FAIMS mode of operation is characterized by conditions where the ion reaches constant velocity relatively quickly compared to the time of the application of the field and the distance the ion travels at constant velocity is large compared to the distance traveled before reaching constant velocity. Accordingly, a compromise condition may be envisaged in which the bath gas pressure between the parallel rods is selected to support operation in both the rf-only mode and the FAIMS mode.

The electric field is usually reported as E/N, where E is the field in volts/cm and N is the number density of the gas. For convenience this is reported in Townsend (Td) units, the E/N adjusted by a factor of $10^{17}$. For example, at 760 torr the number density is about $2.5 \times 10^{19}$, and a field of 12300 volts/cm yield an E/N equivalent to about 50 Td. Note also that at 1 torr a field of 50 Td is about 16 volts/cm. At 50 Td the ion velocity is constant and independent of pressure, assuming that ion mobility varies with pressure as $K_0(760/P)$ where $K_0$ is the mobility at 760 torr, and P is the bath gas pressure. This makes the unit of Td convenient to describe mobility changes with electric field strength, i.e. the energetics of collisions between the gas and the ion are independent of pressure at a fixed value of E/N.

Temperature and pressure both affect N, the number density of the gas. Unlike pressure, temperature also affects the mobility of the ion. As described by Mason and McDaniel in their book "Transport properties of Ions in Gases" (Wiley 1988) the temperature has an effect on mobility that is related to the energy of collisions of the ion with the molecules of the bath gas. When the ion is traveling under the influence of an electric field, the effective temperature experienced by the ion deviates from the temperature of the bath gas. This change of mobility caused by change of effective temperature is analogous to the change in mobility that occurs when the bath gas changes temperature. In both cases the ion experiences collisions with higher energy as the temperature increases.

Note also that temperature affects the average velocity of molecules in the gas, and rates of diffusion. The focusing effect in cylindrical FAIMS tends to move the ions to a localized region in space, but the effects of diffusion, space charge ion-ion repulsion and gas turbulence prevent all of the ions from accumulating in small regions, and the ions are actually distributed in space around this ideal focus point. If the effects of diffusion are lower, at lower temperature, the ions may accumulate in a smaller region of space than at higher temperature, where these comparisons are made with equal focusing strengths through virtual or real electric fields. Similarly, a cloud composed of higher density of ions will occupy a larger region in space than a low density cloud, because the electric charges of the ions creates an electric field that may act in opposition to the focusing action of FAIMS and therefore push the ions away from each other.

It is well known that the rf-only quadrupole, and the mass analysis quadrupole, will function well at low pressures (for example $10^{-7}$ torr), but will totally fail at pressures above 200 torr. All efforts to use these and other related rf devices at 760 torr have failed.

It is also known that FAIMS will function well at 760 torr, and cannot work at $10^{-7}$ torr, where the mean free path between collisions with the gas molecules greatly exceeds the dimensions of the spaces between the electrodes.

In order to function, quadrupoles (and hexapoles, octopoles etc.) require low gas pressures where the ion motion is dominated by momentum. After application of an accelerating force to the ion, the velocity thus acquired remains unchanged in magnitude and direction, unless another force modifies this motion. The motion of an ion in a quadrupole is similar to a marble rolling in a friction free bowl, where the marble may roll quickly along the bottom, and momentum carries it up a side until the kinetic energy is converted to potential energy, or kinetic energy in another direction. This motion is not possible when collisions with the gas remove kinetic energy from the ion, or in the case of the marble rolling in a bowl filled with water where the friction slows the marble until it sits stationary at the bottom of the bowl. These devices work well at low pressures, and gradually deteriorate in function until the gas density causes total failure. This degradation of performance occurs over a range of pressures.

Similarly, FAIMS functions at high pressures, and the function begins to deteriorate at low pressure. At very high pressure, 760 torr for example, the instantaneous application of an electric field causes the ion to accelerate, but in a short time (nanoseconds) the ion reaches a balance where the force from the field exactly matches the magnitude of the 'friction' originating from collisions with the gas causing the ion to reach a constant terminal velocity. As the pressure is lowered, and assuming a fixed field of 50 Td (for example), the time required for the ion to reach this terminal velocity is lengthened. If the applied asymmetric waveform is 1 MHz, a delay of less than $10^{-9}$ sec for ion acceleration to a constant velocity has minimum consequence to the operation of FAIMS. However, if the ion requires 0.1 μsec or 0.5 μsec to achieve constant velocity, the behavior of the ion no longer is identical to that in the previous example. This is not to say that some component of FAIMS behavior no longer exists, but rather it is now modified.

At its fundamental basis the FAIMS behavior still exists at lower pressures where the only change in the nature of the collisions is a decrease in their frequency of occurrence. Although the concept of ion mobility assumes reaching terminal velocity very quickly, this is not an absolute necessity for the present invention. More important than the time necessary to reach terminal velocity is how this terminal velocity is affected by the field strength. If the waveform exposes the ion to a field of 50 Td for a short time in a first direction and a longer period at 25 Td in an opposite direction, the change in 'ion mobility' upon which FAIMS is defined remains functional irregardless of the pressure. If the ion terminal velocity at 760 torr was 5% higher at 50 Td than at 25 Td, this change is present at 100 torr, 10 torr and at 1 torr.

Consider some more details about the conditions at a pressure of 1 torr, and E/N of 50 Td. The applied field at 1 torr is only 16 volts/cm, and the mean free path is $5 \times 10^{-3}$ cm. The time to reach terminal velocity is approximately 2 $mv_d/qE$, where m is the mass (kg), $v_d$ is expected terminal velocity (m/sec), q is the charge (coul) and E is the field (volts/m). The time to reach terminal velocity is about 0.5 μsec for m/z 200 with K=2 at Standard Temperature and Pressure (STP). The motion of the ion therefore includes a period of acceleration in a first direction, followed by deceleration when the field changed polarity, and acceleration in the second direction followed by deceleration again. The periods of time of acceleration are equal if the final velocity of the ion is based on an ion mobility that is independent of E/N. The period of time of acceleration in high field and low field will differ if the ion mobility is dependent on E/N (the normal situation in FAIMS). This difference in mobility at low and high field translates into two effects: (i) the final terminal velocity, thus distance traveled and (ii) the time required to achieve terminal velocity, also having effect on distance traveled. If the distance traveled during high and low field portions of the waveform are not equal, the equivalent of CV, i.e. a dc offset voltage, will be required to ensure that the ion does not collide with an electrode. The time necessary to achieve terminal velocity is also dependent on the mass of the ion. In other words the CV applied will reflect the m/z of the ion at low pressure. This is because the delay in reaching terminal velocity will require adjustment of CV since the time to reach terminal velocity results in a decrease in the total distance traveled by the ion. This decrease is more significant during the high voltage component of the waveform, which lasts for a shorter time. For example, if the distance traveled during the high voltage period of the waveform would have been 0.1 mm without a period of acceleration, and 0.09 mm because of lost distance during acceleration and 0.1 mm and 0.095 mm respectively during the low voltage period of the waveform, a net drift of the ion will occur. This net drift, as was the case in conventional FAIMS operation, must be compensated for by a dc voltage applied between the electrodes, for the purpose of maintaining ion transmission. The dc voltage will now be a function of both the m/z of the ion and of the change of mobility at high field relative to low field. The recognition of the importance of pressure during the transition from high pressure FAIMS-only mode to low pressure where the momentum of the ion contributes to the motion is critical for understanding the present invention.

In WO 01/69647, the instant inventor disclosed operation of the quadrupole assembly in FAIMS mode when a FAIMS based separation of ions is desired, and operation of the quadrupole assembly in rf-only mode when a FAIMS based separation is not required. In this way, the FAIMS analyzer portion is effectively "electronically removed" from the system when not in use.

Unfortunately, the ions entering the space between the quadrupole assembly, as described in WO 01/69647, may have several electron volts (eV) of translational energy and may be transmitted through the quadrupole assembly in a very short time. Accordingly, the residence time of the ions within the quadrupole assembly may be short and the separation period may be insufficient to achieve an acceptable FAIMS-based separation.

It is an object of the instant invention to provide a method and apparatus that overcomes the limitations of the prior art.

SUMMARY OF THE INVENTION

In accordance with an aspect of the instant invention there is provided a method of separating ions comprising the steps of: providing an analyzer region that is operable in both an rf-only mode and in a FAIMS mode; introducing ions into the analyzer region; effecting a selective separation of the ions within the analyzer region substantially during operation in the FAIMS mode; and, extracting ions from the analyzer region substantially during operation in the rf-only mode.

In accordance with another aspect of the instant invention there is provided a An apparatus for separating ions comprising: a set of parallel rods having a space therebetween, the space having first and second ends and defining an analyzer region; and, an electrical controller for electrically coupling to the set of parallel rods, for applying at least an rf-voltage between the parallel rods of the set of parallel rods in a first operating mode and for applying a combination of an asymmetric waveform voltage and a direct current voltage between the parallel rods of the set of parallel rods in a second operating mode.

BRIEF DESCRIPTION OF THE DRAWINGS

Exemplary embodiments of the invention will now be described in conjunction with the following drawings, in which similar reference numbers designate similar items.

DETAILED DESCRIPTION OF THE INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
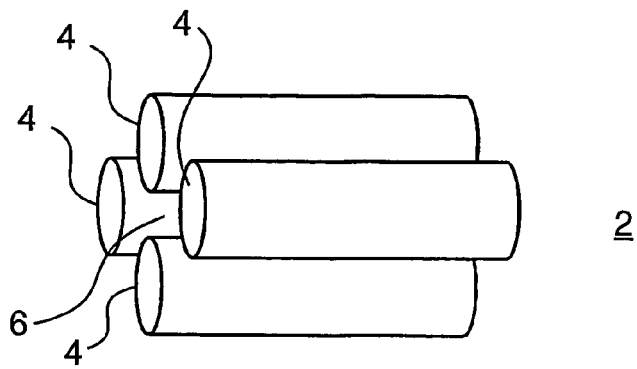
FIG. 1 shows an isometric view of a multiple parallel rod assembly including four parallel rods for use with an apparatus according to an embodiment of the instant invention.

Referring to FIG. 1, shown is an isometric view of a multiple parallel rod assembly having a quadrupole configuration. The quadrupole assembly, shown generally at 2 in FIG. 1, includes four parallel rods 4 having a space therebetween, the space having first and second ends and defining an analyzer region 6. By the application of appropriate voltages to the four parallel rods 4 using a not illustrated electrical controller, the analyzer region 6 is operable in an rf-only mode, and a FAIMS mode, as well as a combination of these two modes.

The four parallel rods 4 shown in FIG. 1 are round rods, which are used to approximate the four parallel spaced hyperbolic surfaces that are strictly required to establish a two-dimensional quadrupole field. Of course, optionally four parallel spaced hyperbolic surfaces are provided in place of the round rods. Further optionally, the four parallel rods 4 include a conductive outer surface carried on an electrically insulating material. Further optionally, the four parallel rods 4 are hollow.

Figure 2A:
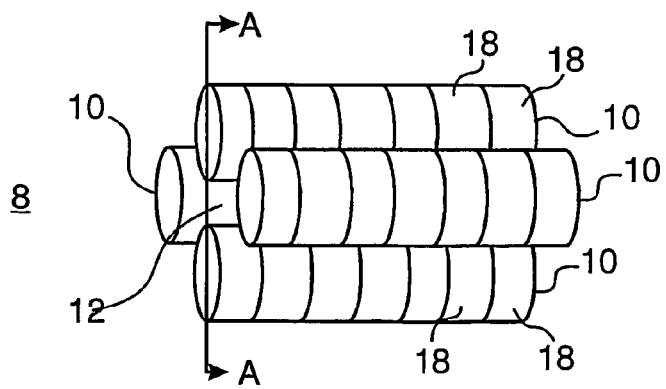
FIG. 2a shows an isometric view of a multiple parallel rod assembly including four parallel segmented rods for use with an apparatus according to an embodiment of the instant invention.

Referring now to FIG. 2a, shown is an isometric view of another multiple parallel rod assembly having a quadrupole configuration. The quadrupole assembly, shown generally at 8 in FIG. 2a, includes four parallel segmented-rods 10 having a space therebetween, the space having first and second ends and defining an analyzer region 12. In the example discussed below, the application of appropriate voltages to the four parallel segmented-rods 10 using a not illustrated electrical controller is used to operate the analyzer region 12 in either one of an rf-only mode and a FAIMS mode. Each rod 10 includes a plurality of individual segments 18. Some of the individual segments 18 have been explicitly labeled on two of the segmented-rods 10 in FIG. 2a. Labels for other individual segments 18 in FIG. 2a have been omitted in order to preserve clarity. Optionally, not illustrated electrically insulating spacers are used to separate adjacent individual segments 18 of a same segmented-rod 10. An example of a suitable material for forming the electrically insulating material is PEEK. Electrically isolating the individual segments 18 of the segmented rods 10 supports application of different dc potentials between different sets of individual segments 18 of the quadrupole assembly 8. This allows a potential gradient or a potential well to be established along the length of the quadrupole assembly 8, which may advantageously be used to manipulate the trajectories of ions within the analyzer region.

Figure 2B:
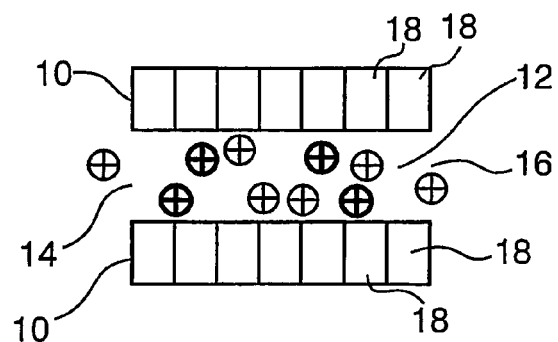
FIG. 2b shows a cross sectional view of the multiple parallel rod assembly of FIG. 2a taken along the line A-A.

Referring now to FIG. 2b, shown is a cross sectional view of the quadrupole assembly 8 of FIG. 2a taken along the line A-A. Since such a section misses two of the segmented-rods 10, the cross section appears to be similar to that of two parallel plates. It is important to note that in regards to the behavior of ions there is little similarity between the quadrupole rods, and flat plates. Ions are shown to enter the analyzer region 12 between the segmented-rods 10 at a first end 14 thereof, and to move through the analyzer region 12 in a direction toward a second end 16 thereof. In this example the ions are assumed to lack significant translational energy in a direction along the length of the segmented-rods 10. However, typically the ions may have several eV of translational energy and may be transmitted through the quadrupole assembly 8 in a very short time.

Figure 3:
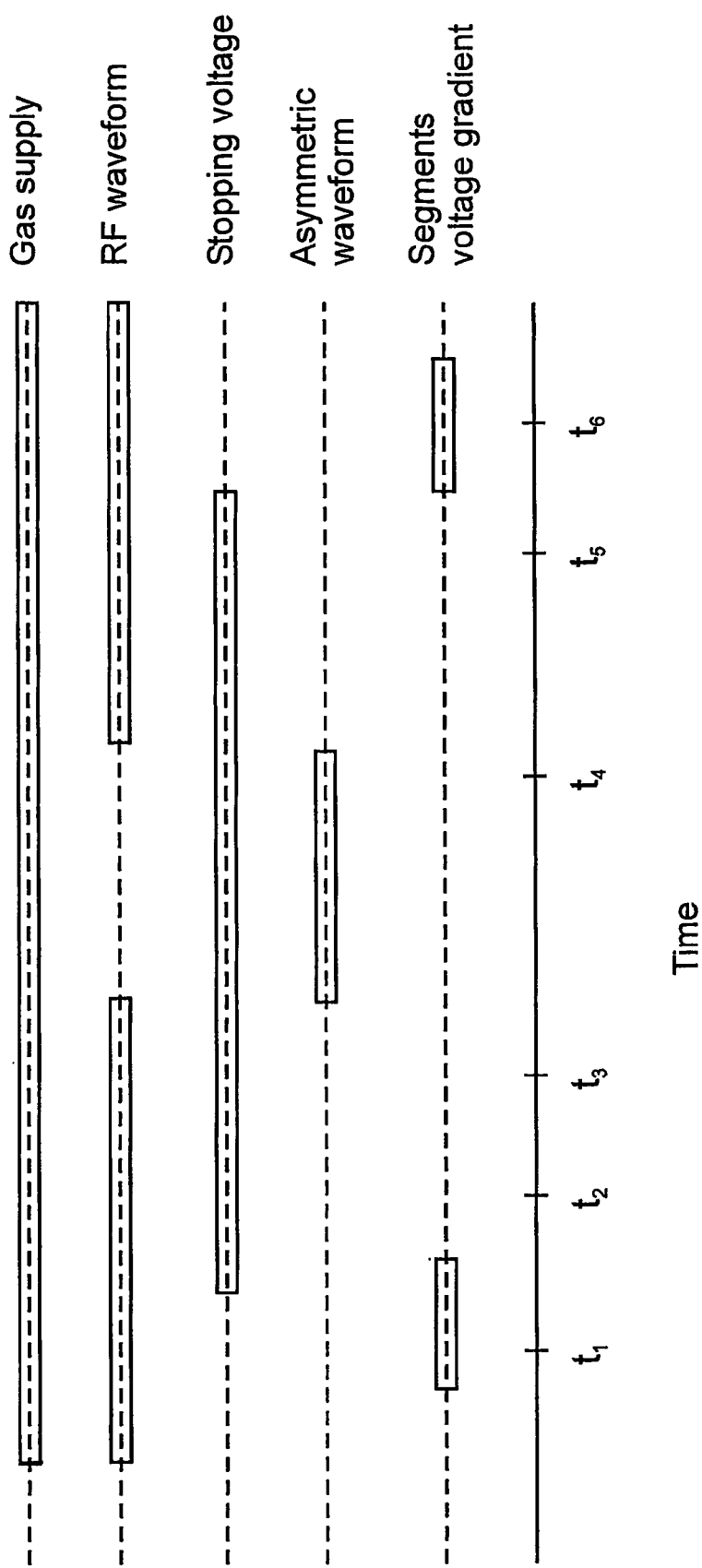
FIG. 3 is a schematic illustration showing the application of various electrical signals to an analyzer according to an embodiment of the instant invention, at a series of times $t_1$ to $t_6$.

FIG. 3 shows one possible set of operating parameters for the quadrupole assembly 8 of FIG. 2a. A constant gas supply is maintained through the analyzer region 12. Waveform voltages and dc voltages are applied at different times to cause changes in the motion of the ions entrained in the analyzer region 12 and to change from rf-only mode to FAIMS mode. Operating conditions at times $t_1$ to $t_6$ are shown to assist in the discussion of FIGS. 4a to 4f.

Referring now to FIGS. 4a to 4f, shown are a series of cross sectional views of an analyzer according to an embodiment of the instant invention at different times $t_1$ to $t_6$. FIGS. 4a to 4f are shown to illustrate by way of a specific and non-limiting example the operation of an analyzer according to an embodiment of the instant invention. In the instant non-limiting example, a process is described involving the application of sinusoidal waveforms and asymmetric waveforms to effect both rf-only and FAIMS modes of operation.

Figure 4A:
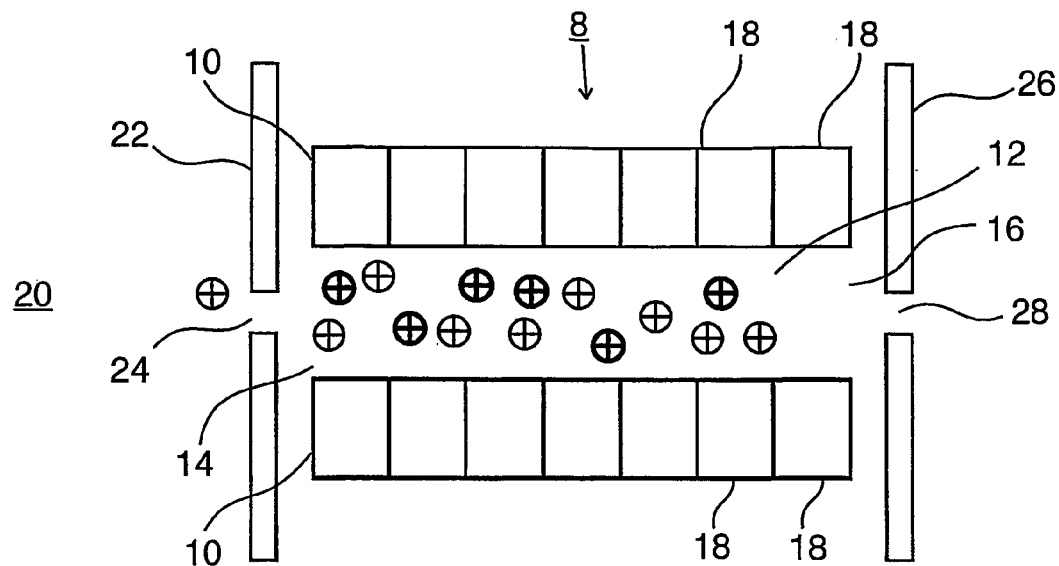
FIG. 4a shows a cross sectional view of an analyzer according to an embodiment of the instant invention at a time $t_1$.

Referring now specifically to FIG. 4a, the analyzer according to an embodiment of the instant invention is shown generally at 20. The analyzer 20 includes, in this specific example, the quadrupole assembly 8 of FIG. 2a, including four parallel segmented-rods 10, of which two segmented-rods 10 are illustrated and two segmented-rods 10 are not illustrated. A space between the four parallel segmented-rods defines an analyzer region 12 having a first end 14 and a second end 16. Disposed adjacent the first end 14 is an ion entrance lens 22 having an ion inlet 24 defined therein for introducing ions that are produced at a not illustrated ion source into the first end 14 of the analyzer region 12. Similarly, disposed adjacent the second end 16 of the analyzer region 12 is an ion exit lens 26 having an ion outlet 28 defined therein for supporting extraction of ions from the second end 16 of the analyzer region 12. The quadrupole assembly 8, the ion entrance lens 22, and the ion exit lens 26 are electrically coupled to a not illustrated at least an electrical controller. A not illustrated housing also surrounds and supports the analyzer 20. The housing includes at least a port for providing a predetermined atmosphere within the housing and within the analyzer region 12.

Referring still to FIG. 4a, the analyzer 20 is shown at a time $t_1$ of FIG. 3. The potential applied to the ion entrance lens 22 is selected to allow ions to pass through the ion inlet 24 and into the first end 14 of the analyzer region 12. Appropriate voltages are applied to the quadrupole assembly 8 for operating the analyzer region 12 in the rf-only mode during the time that the ions are being introduced. Optionally, the potential applied to the ion exit lens 26 is selected to either retain ions within the analyzer region 12 or to allow the ions to escape through the ion outlet 28. Segment voltages may be applied to draw ions along the length of the assembly.

Figure 4B:
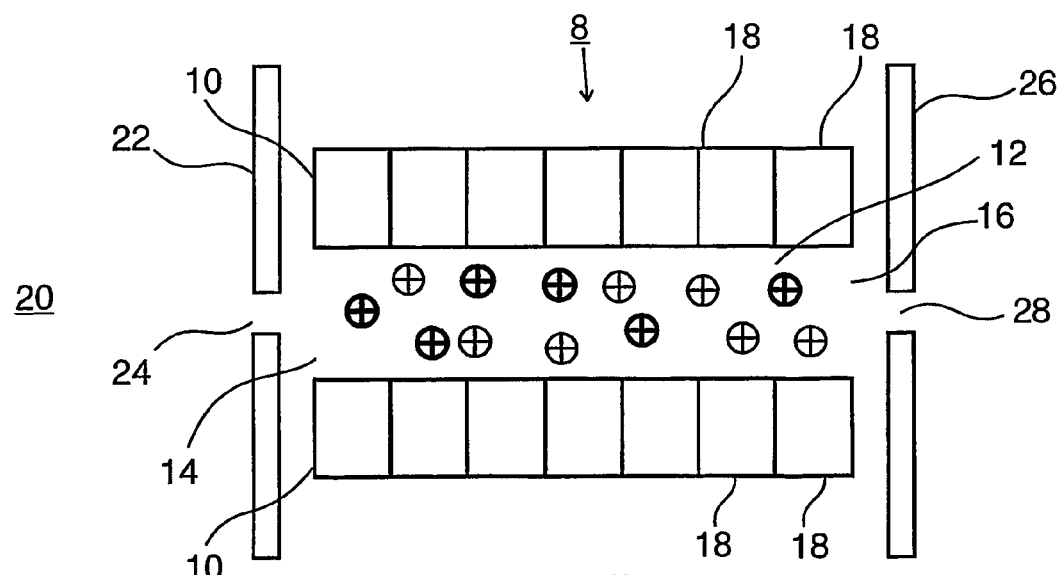
FIG. 4b shows a cross sectional view of the analyzer of FIG. 4a at a time $t_2$.

Referring now to FIG. 4b, shown is the analyzer 20 at a time $t_2$. The potentials applied to the ion entrance lens 22 and the ion exit lens 26 are set to values that are appropriate for trapping the ions within the analyzer region 12 between the first end 14 and the second end 16. These potentials are referred to throughout this disclosure as "stopping potentials." All the segments of the segmented rods are at the same dc potential, i.e. no gradient.

Figure 4C:
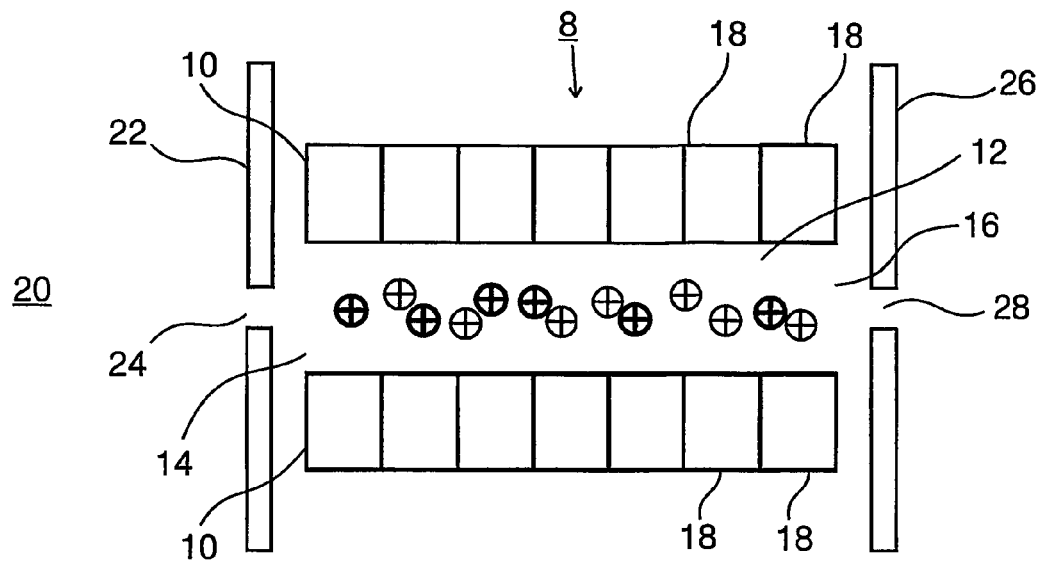
FIG. 4c shows a cross sectional view of the analyzer of FIG. 4a at a time $t_3$.

Referring now to FIG. 4c, shown is the analyzer 20 at a time $t_3$. If a bath gas is present within the analyzer region 12 at a suitable pressure, and the quadrupole assembly 8 is operated in rf-only, mode, then the trapped ions which were distributed in various locations between the rods at time $t_2$ are "cooled" as a result of collisions with the bath gas molecules, and move to the center axis as shown at FIG. 4c.

Figure 4D:
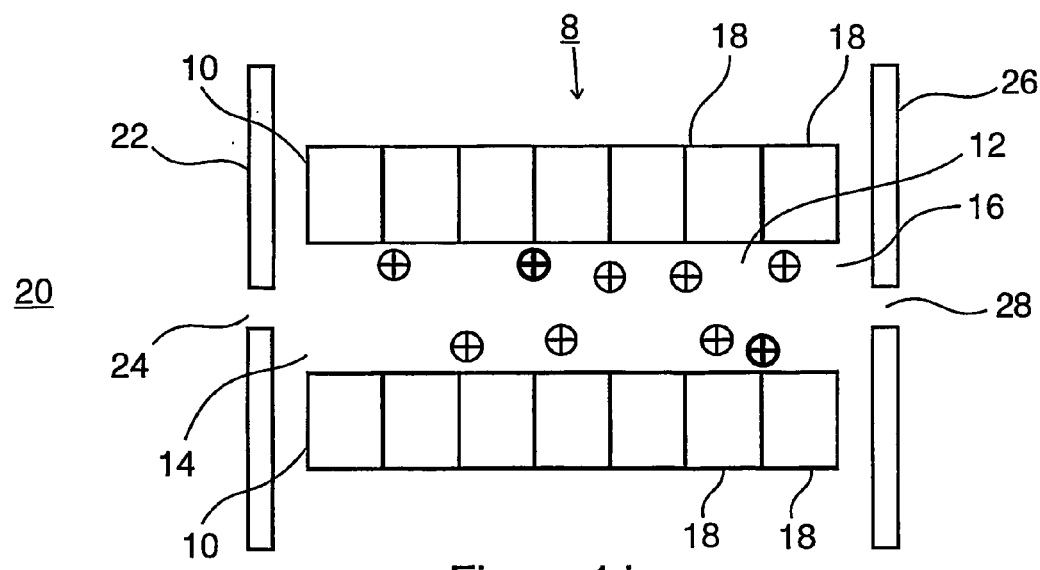
FIG. 4d shows a cross sectional view of the analyzer of FIG. 4a at a time $t_4$.

Referring now to FIG. 4d, shown is the analyzer 20 at a time $t_4$. As shown in FIG. 3, at time $t_4$, the voltages applied to the quadrupole assembly 8 are changed to effect a FAIMS mode of operation. For the FAIMS mode of operation, many optional methods of application of the asymmetric waveform are possible. For example, three rods are operated with a first dc voltage, while the asymmetric waveform voltage and a second dc voltage are applied to the fourth rod. In another example a first dc voltage is applied to a pair of opposite rods and the asymmetric waveform and a second dc voltage are applied to the remaining two rods. In yet another example a first dc voltage is applied to a pair of adjacent rods and the asymmetric waveform and a second dc voltage are applied to the remaining two adjacent rods. Regardless of the way in which the asymmetric waveform voltage and the compensation voltage are applied between the electrodes, the method described here requires that the separation of ions takes place because of the difference in mobility of various ions in electric fields (E/N) that are strong and electric fields that are weak. The FAIMS method requires that the fields (E/N) that the ions experience are strong in a first direction and subsequently weak in the opposite direction with the durations of time selected so that if the ion mobility was independent of the field strength the ion would arrive back at the same location at the end of one complete cycle of the waveform. If E/N is high enough that the mobility does not remain constant, the ion will drift because of the net difference in distance traveled during the forward and reversed directions of travel.

Referring still to FIG. 4d, at time $t_4$ the ions drift away from the center axis at rates of motion that are dependent on the relative mobility of the ion in high and low fields. The application of a compensation field creates a balanced condition for some ions so that they do not collide with the rods. This compensation field is used to separate the ions at time $t_4$, so that after a balanced FAIMS operating mode is achieved the remaining ions are a subset of the mixture of ions originally in the rods at time $t_1$.

Figure 4E:
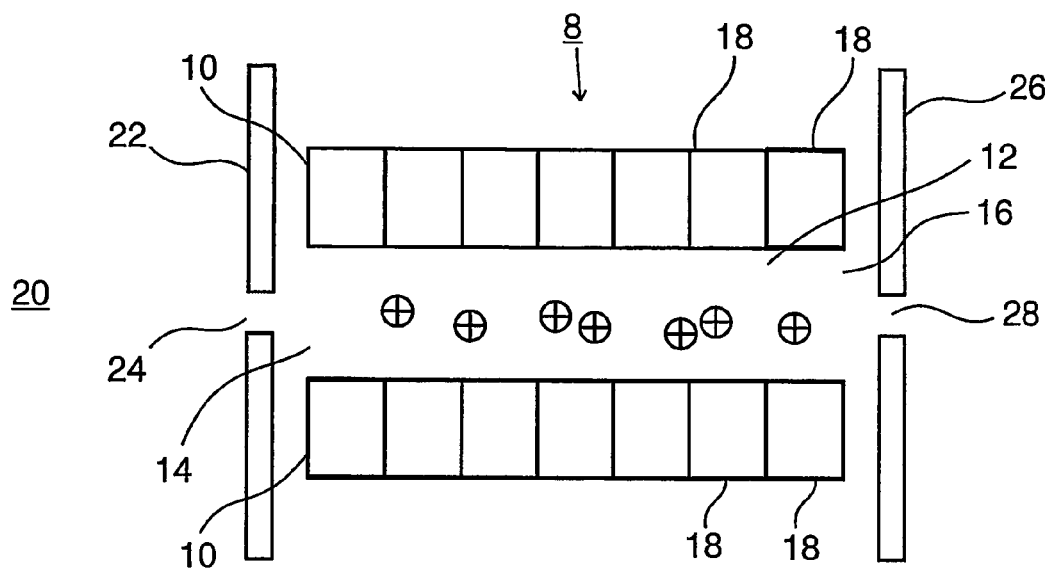
FIG. 4e shows a cross sectional view of the analyzer of FIG. 4a at a time $t_5$.

Referring now to FIG. 4e, shown is the analyzer 20 at a time $t_5$. At time $t_5$, the voltages applied to the quadrupole rods are returned to their original rf-only operating state. The ions which were in a balanced condition or were drifting towards the segmented-rods 10 as a result of the asymmetric waveform and compensation voltage are returned to the center axis of the quadrupole assembly 8 due to collisional cooling. This minimizes further loss of the ions by returning them to a virtual potential well in the middle of the quadrupole assembly 8.

Figure 4F:
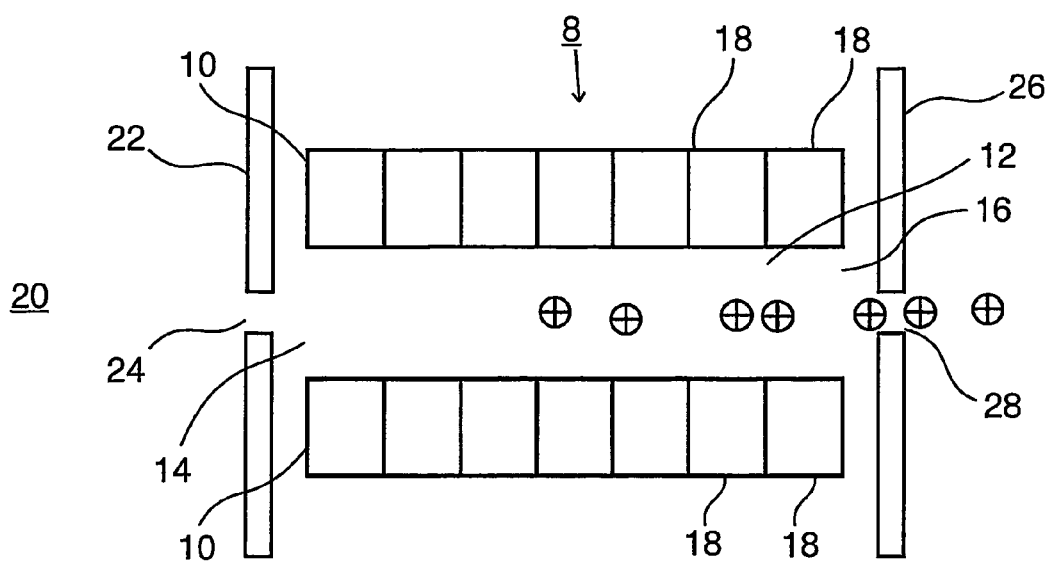
FIG. 4f shows a cross sectional view of the analyzer of FIG. 4a at a time $t_6$.

Referring now to FIG. 4f, shown is the analyzer 20 at a time $t_6$. For instance, the ions are subjected to a longitudinal gradient electric field by application of different dc voltages to the segments of the quadrupole assembly 8, and the ions drift from the assembly through the exit lens. Advantageously, the step of collisional cooling performed at time $t_5$ returns the ions to the center axis of the quadrupole assembly 8, thereby collimating the ions and improving ion extraction efficiency through the ion outlet 28.

Optionally, the process of applying rf-only followed by the FAIMS voltages is repeated, especially if the ions are trapped within the analyzer region 12 of the quadrupole assembly 8 by stopping potentials applied via the ion entrance lens 22 and the ion exit lens 26. Repetitive application has the benefit of maintaining the benefit of the potential well caused by the rf-only mode of operation. The FAIMS fields may have virtual minima but these may not be located at the center of the assembly. The ions may alternatively be moved from the virtual well caused by the rf-only mode of operation and the potential well caused by the FAIMS focusing effect. This will be considered further in the discussion below.

In an optional embodiment, segmented rods are used without the ion entrance lens 22 and ion exit lens 26. In this embodiment, the ions are not trapped in the analyzer region 12 but may instead leak out of either end. Some control over the trajectories of the ions may be realized by the application of different dc potentials to different individual segments 18 of the segmented-rods 10. In this way, a potential gradient within the analyzer region may be established for accelerating and decelerating ions, etc. The ions may also be trapped in this assembly by the application of dc voltages to the segments to produce a potential well midway between the first and last segment.

In yet another optional embodiment, unsegmented rods as described with reference to the quadrupole assembly 2 of FIG. 1 are used, either with or without the ion entrance lens 22 and ion exit lens 26. In this optional embodiment, the analyzer is cycled from the rf-only mode to the FAIMS mode and back to the rf-only mode while the ions are moving through the analyzer region between the first end and the second end.

Figure 5A:
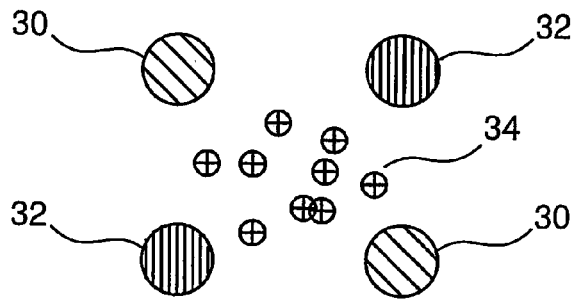
FIG. 5a shows an end-on view of an ensemble of ions after introduction into a quadrupole assembly similar to the ones shown at FIG. 1 and FIG. 2.

Referring now to FIG. 5a, shown is an end-on view of an ensemble of ions 34 contained within a quadrupole assembly similar to the ones shown at FIG. 1 and FIG. 2. In FIG. 5a, two opposite rods 30 are electrically coupled one to the other to form a first pair of rods, and the remaining two rods 32 are electrically coupled one to the other to form a second pair of rods. The voltages that are applied between the two rods 30 and the two rods 32 in FIG. 5a are for conventional operation in rf-only mode. In particular, the two rods 30 and the two rods 32 are maintained at the same dc voltage in rf-only mode. FIG. 5a represents a situation in which the ions, having been introduced into the space between the rods 30 and the rods 32, have had insufficient time to undergo collisional cooling to arrive near the central axis of the rods.

Figure 5B:
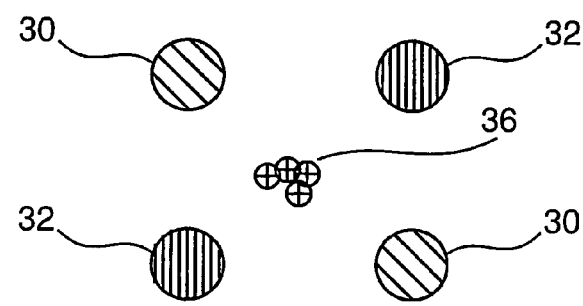
FIG. 5b shows an end-on view of a subset of the ensemble of ions within a quadrupole assembly similar to the ones shown at FIG. 1 and FIG. 2, and subsequent to a period of collisional cooling.

Referring now to FIG. 5b, shown is an end-on view illustrating a subset 36 of the ensemble of ions 34 within a quadrupole assembly similar to the ones shown at FIG. 1 and FIG. 2, and subsequent to a period of collisional cooling. For instance, if the rods 30, 32 are in a low pressure bath gas, for example a few millitorr, then the ensemble of ions 34 eventually converges to the central axis of the rods due to loss of energy by collisions with the bath gas molecules. After a cooling period, the ions whose trajectories are stable under the conditions of rf voltage and frequency tend to be found near the central axis of the rods as shown in FIG. 5b. The ions whose trajectories are stable under the conditions of rf voltage and frequency form the subset 36, whilst other ions of the ensemble of ions 34 are lost.

Figure 5C:
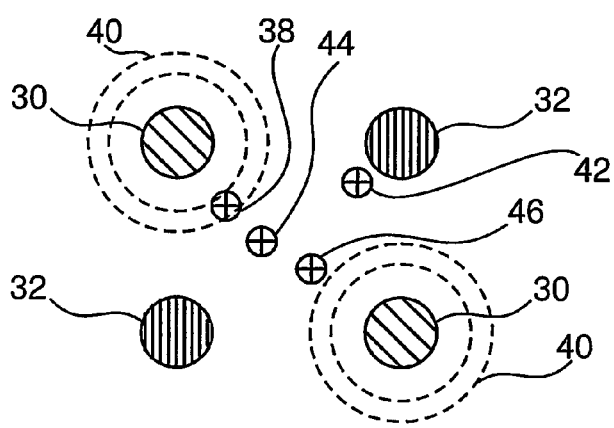
FIG. 5c shows an end-on view of a subset of the ensemble of ions within a quadrupole assembly similar to the ones shown at FIG. 1 and FIG. 2, and during operation in FAIMS mode.

Referring now to FIG. 5c, shown is an end-on view illustrating a subset 36 of the ensemble of ions within a quadrupole assembly similar to the ones shown at FIG. 1 and FIG. 2, and during operation in FAIMS mode. As is practice in any FAIMS system, the asymmetric waveform voltage and the dc voltages are set to select conditions of E/N and compensation fields for establishing a balanced condition for an ion with appropriate mobility behavior as a function of field strength, for instance an ion 38 of the subset of ions 36. Around electrodes 30 a balanced condition is established, shown by dotted lines 40, at which the selected ion 38 neither migrates toward the rod 30 or away from the rod 30. This region 40 is the focusing region previously discussed in regard to behavior of ions in a FAIMS system.

Referring still to FIG. 5c, it is shown that the ions of the subset 36 drift away from the central axis of the rods during operation in FAIMS mode, as they oscillate under the influence of the asymmetric waveform due to the differences in their ion mobility under conditions of low and high E/N. Some ions 38 "fall" into a potential well defined by the FAIMS focus region 40. Other ions for which the waveform voltage and compensation fields are other than appropriate will move to other locations. For example some ions 42 drift and collide with the rods 32. Other ions 44 and 46 drift slowly, or find balanced conditions that differ from those of ions 38. Alternatively, the asymmetric waveform can be applied to 1, 2, or 3 of the rods forming the quadrupole. The region where ion focusing occurs will change accordingly.

Figure 5D:
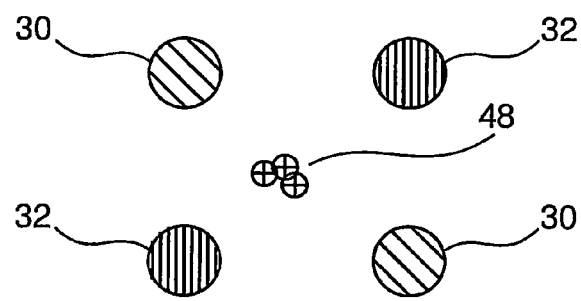
FIG. 5d shows an end-on view of a second subset of the ensemble of ions within a quadrupole assembly similar to the ones shown at FIG. 1 and FIG. 2, and subsequent to a second period of collisional cooling.

After the conditions shown in FIG. 5c have been applied for a period of time, the sinusoidal wave used for rf-only operation of the quadrupoles is restored, and the remaining ions 48 move to the center axis as shown in FIG. 5d. It may be advantageous to alternate between these conditions for a number of cycles. In this instance, it may be further advantageous to operate the different cycles of FAIMS mode at different compensation voltages to obtain greater separation of the ions.

Recall that some ions collide with the electrodes and these ions are lost. The FAIMS separation therefore leaves a sub-set of the original ions within the electrodes. Also note that this sub-set of ions may not be defined as the same sub-set of ions that might be found after operation of FAIMS of other electrode geometries. For example, parallel plate FAIMS electrodes operated under similar conditions of E/N, waveform voltages, compensation fields, waveform frequency, temperature and gas pressure, may not result in the same sub-set of ions. This will be due to two factors, which are dependent on electrode geometry: the resolution of the separation of the ions, and the focusing ability of the electrode assembly. Note that the electrode geometry of FIG. 5a to 5d may retain ions whose motion (low mobility) is very low even though the conditions may not favor focusing or a balanced condition for this particular type of the ions. The subset of ions will also be a function of the periods of time during which the quadrupole rod set is operated in rf-only mode and in FAIMS separation mode. These relative periods of time were not present or were not applicable to flat plate FAIMS (or many other FAIMS geometries) considered in the prior art.

The details of the electronic methods for application of the sinusoidal waves or the asymmetric waveform have not been considered. In fact, a plurality of possible approaches may be envisaged. In every case, the time that is required for transition between the rf-only mode and the FAIMS mode is in practice other than zero. It is therefore important that the electronic transitions be controlled in a manner to avoid loss of ions to the walls of the electrodes. For example, removal of the waves and waveforms with remaining dc voltages in place results in loss of the ions. Accordingly, the waveform transitions should be synchronized with changes in dc voltages. Note also that at lower gas pressures, the ion mobility is very high and the ions may respond to the fields quite rapidly. Therefore the transitions between modes of operation must be controlled carefully.

In a first approach to managing the waveforms, the sinusoidal waves of the two frequencies used to form the FAIMS asymmetric waveform are applied to the rods in an independent fashion. For example, one of the sinusoidal waves is already on the quadrupole assembly, e.g., for purposes of operation in rf-only mode, and the second sinusoidal wave of higher or lower frequency is added by ramping the amplitude of this second wave from zero to the target amplitude. After the selected period of time the amplitude of this second wave is ramped back to zero leaving the original sinusoidal wave, which then forms part of the voltages applied during rf-only mode of operation. During the ramp up and ramp down of the amplitude of the second wave, the applied dc voltages are also ramped in a manner to maintain conditions (e.g. focus region) to avoid loss of an ion of interest.

In a second approach for control of the transitions between rf-only and FAIMS modes of operation, the component sinusoidal waves are always present on the rods, but in phase relationships that do not give the FAIMS separation. Certain values of the phase shift, such as for example zero radians, may result in a waveform that is symmetric rather than asymmetric. A controlled change of the phase angle is used to convert to FAIMS operation. The gradual change in phase angle between the two sinusoidal waves allows the applied waveform to be converted smoothly to the desired asymmetric shape. The appropriate dc levels are applied in synchronization with the phase shifts in order to maintain balanced conditions (FAIMS operation), or at low levels of asymmetry, to maintain rf-only operation.

Figure 6A:
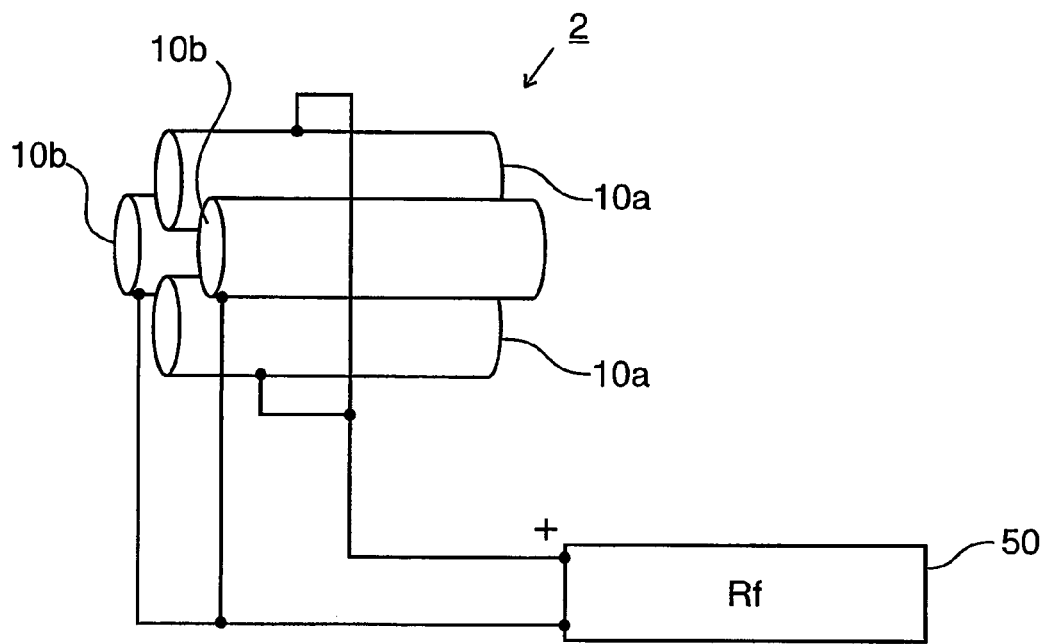
FIG. 6a shows the quadrupole assembly of FIG. 1 having diagonally opposite rods connected to the positive and negative outputs of an electrical controller.
Figure 6B:
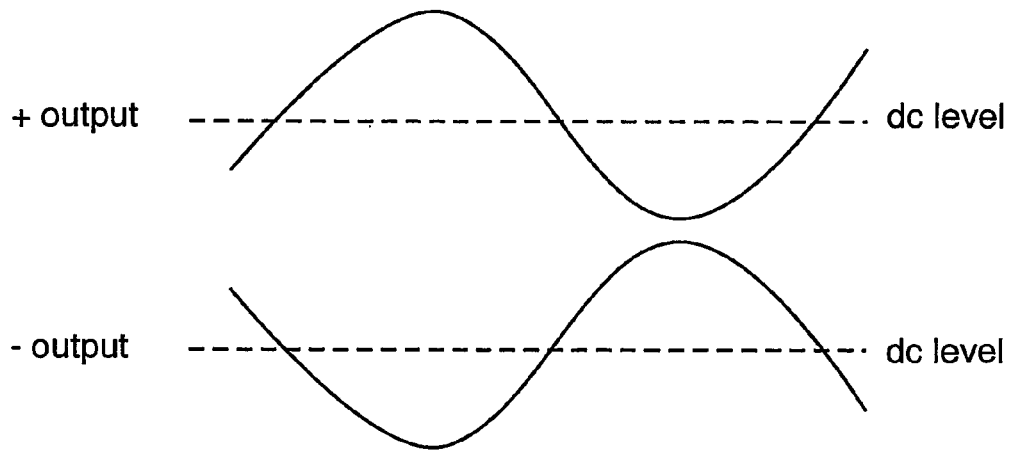
FIG. 6b shows sinusoidal waves that are 180 degrees out of phase for being applied to the diagonally opposite rods of FIG. 5a in the rf-only mode.

Referring now to FIG. 6a, shown is a quadrupole assembly 2 having diagonally opposite rods 10a and 10b connected to the positive and negative outputs of an electrical controller 50, respectively. For clarity, in operation in rf-only mode, the sinusoidal waves applied to the opposite pairs of electrodes differ in polarity as shown in FIG. 6b. This means the maximum positive voltage is applied by electrical controller 50 to one of the pairs of diagonally opposite rods 10a or 10b at the same time as the maximum negative polarity voltage is applied to the other one of the pairs of diagonally opposite rods 10a or 10b. As such, the center axis of the four rods is at a fixed dc value and the pairs of rods 10a and 10b are alternately held above and below this dc value.

Figure 6C:
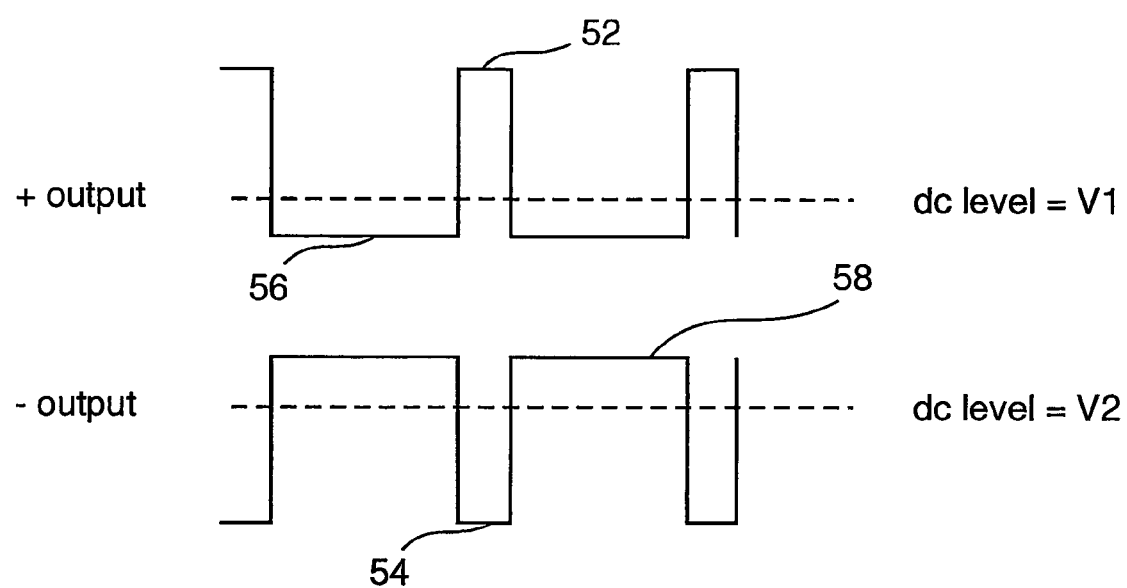
FIG. 6c shows square waves for being applied to the diagonally opposite rods of FIG. 5a in the rf-only mode.
Figure 7A:
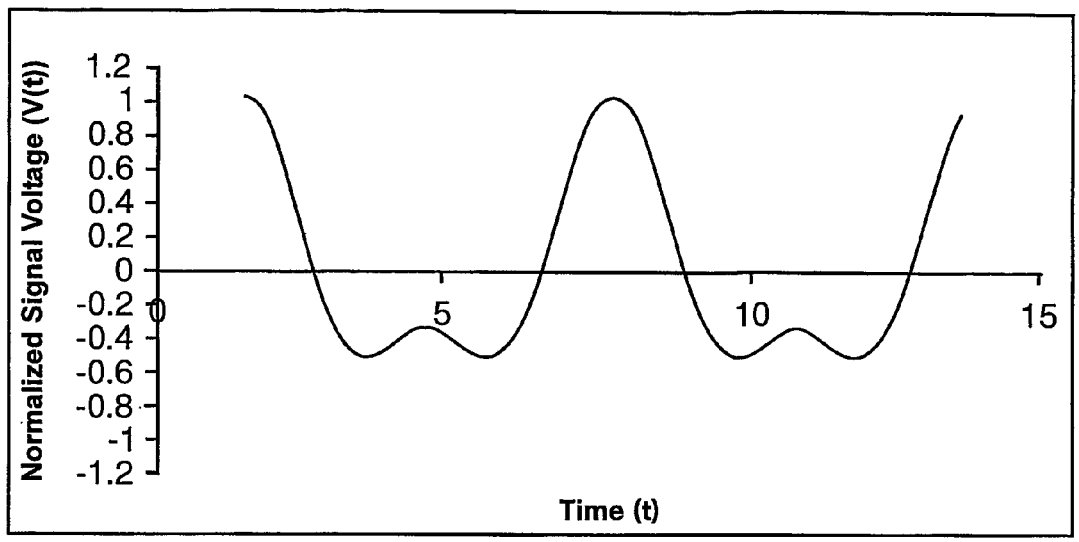
FIG. 7a shows an asymmetric waveform with phase shift of $\pi/2$ radians.
Figure 7B:
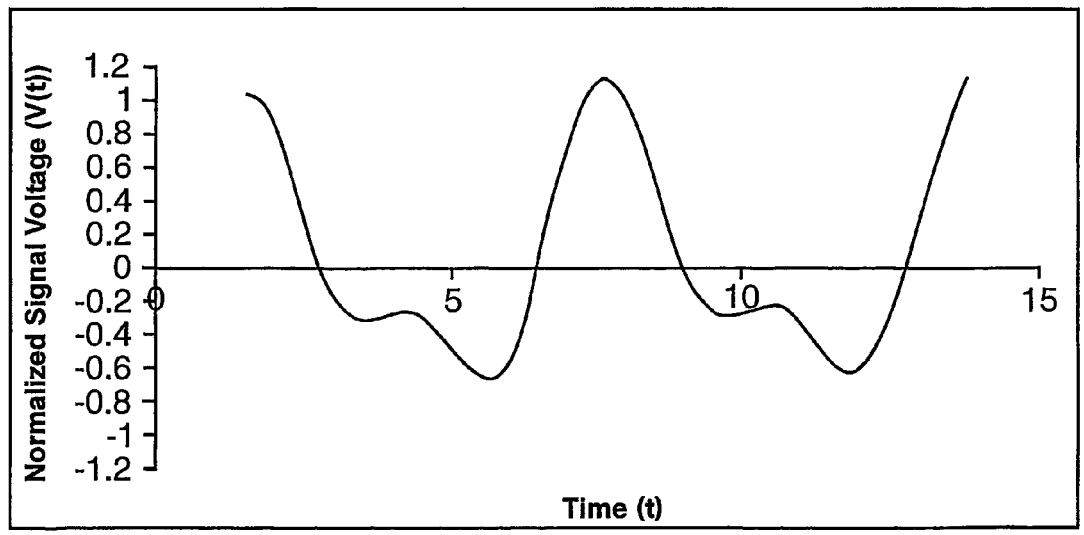
FIG. 7b shows an asymmetric waveform with phase shift of 1.0 radians.
Figure 7C:
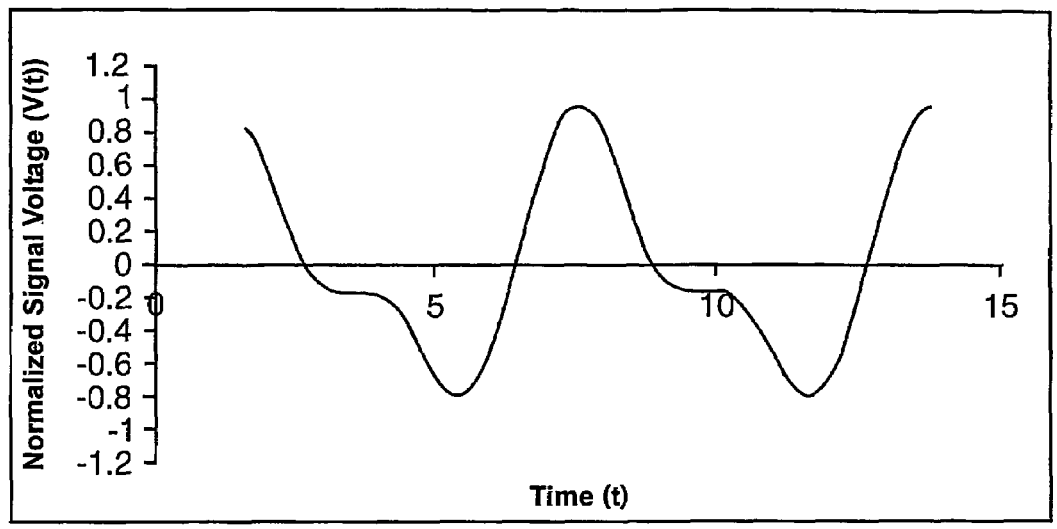
FIG. 7c shows an asymmetric waveform with phase shift of 0.5 radians.
Figure 7D:
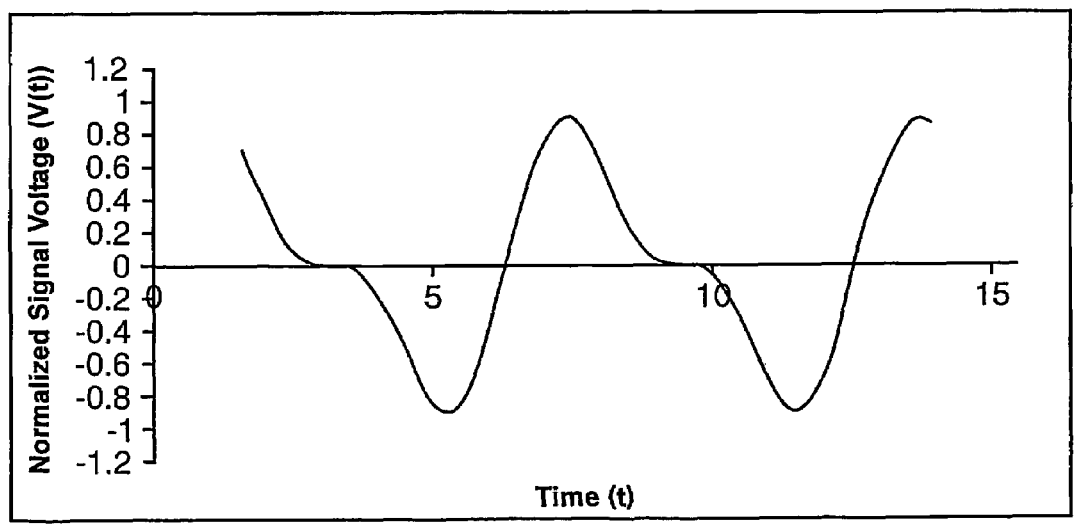
FIG. 7d shows a symmetric waveform with phase shift of 0.0 radians.

Referring now to FIG. 6c, it is shown that it is also possible for the quadrupole assembly 2 to operate in rf-only mode with two asymmetric waveforms applied to the two pairs of rods in the manner described above. Consider the application of asymmetric square waves with a short time of higher voltage and a longer time of opposite polarity lower voltage as shown at FIG. 6c. In a type of rf-only operation this waveform can be applied so that one pair of rods 10a or 10b is at the high maximum voltage 52 in positive polarity while the other pair of rods 10a or 10b are at the same maximum voltage 54 of opposite polarity. The two pairs of rods switch simultaneously to the opposite polarity and one pair is held at the lower voltage 56 and the other pair is at the same voltage 58 of opposite polarity. This establishes the same condition of the center axis remaining at a constant fixed dc potential. In rf-only mode of operation dc level=V1 and dc level=V2 are equal. If V1 and V2 are not equal, the rods operate in mass analysis mode.

In order to illustrate that application of asymmetric waveforms as shown in FIG. 6c will in fact create a FAIMS type of separation, the less complicated case of parallel plate electrode geometry will be considered. As is obvious to one of skill in the art, there are many ways to achieve the introduction of the fields between parallel plates, including the method of holding one plate at a fixed dc voltage while applying the asymmetric waveform to the other plate. This means that the mid-point between the two plates does not stay at the same apparent dc potential. If a constant dc level at the middle point between the plates is required, one plate is positive and the other plate negative relative to this middle dc voltage. Two asymmetric waveforms are applied to the opposite parallel plates using the traces shown in FIG. 6c. Taking the square waveform example, the electric field in a first direction is established by a positive voltage 52 on one plate and a negative voltage 54 on the second plate. Simultaneously both plates change voltage to the opposite polarity, both signal amplitudes being of same absolute value, for example 56 and 58 in FIG. 6c. In other words both plates carry an asymmetric waveform of opposite polarity. Together, the appropriate fields are established between the plates so that the ion between the two places experiences a high field for a short time and a lower field for a longer time. A compensating dc field must also be applied through, for example, the dc offset voltage via a difference of values of V1 and V2 in FIG. 6c, to selectively transmit the ion of interest. It follows that the quadrupole rods in a vacuum can be operable in rf-only mode by application of an asymmetric waveform. At vacuum, the quadrupole rod assembly can be operated in rf-mode by the application of either a symmetric or an asymmetric waveform. At higher pressures, the quadrupole assembly can be operated in FAIMS mode by the application of an asymmetric waveform and a compensation voltage. At intermediate pressures where both modes of operation are supported, the quadrupole assembly of FIG. 6a is operated either in rf-only mode by the application of a symmetric waveform or in FAIMS mode by application of an asymmetric waveform and a compensation voltage by electrical controller 50.

The transition between purely rf-only mode and FAIMS separation mode at intermediate pressures is created, for example, by phase shifts in the two sinusoidal waves that comprise the asymmetric waveform described by equation 1. For example, FIGS. 7a, 7b, 7c, and 7d illustrate the resultant output waveform of the electrical controller with phase shifts of $\pi/2$, 1.0, 0.5, and 0.0 radians, respectively, in the two input sinusoidal waves used to produce the output waveform. The best approximation of an asymmetric square wave is achieved with a phase shift of $\pi/2$ and no asymmetry results with a phase shift of zero radians. In a FAIMS system including parallel flat plates at atmospheric pressure, an ion separation takes place during application of compensation voltage and a waveform generated with phase shift of $\pi/2$, while at the other extreme, no ion separation can be achieved if the waveform is generated with a phase shift of zero radians. On the other hand, when applied to quadrupole rods at low pressure, the symmetric output waveform having a phase shift of zero radians will result in conventional rf-only mode of operation, with mass range and low mass cutoff as appropriate to voltages and frequencies of the sine waves.

Note that the dc voltages appropriate to the FAIMS separation should accompany application of the asymmetric waveform because the application of fields that are asymmetric in time will establish an ion drift towards one of the electrodes. Collision with a wall occurs unless some balancing force is established. In the quadrupole electrode geometry the virtual potential well of the rf-only mode of operation can be used to effect this balancing action. For example if the potential well developed in rf-only mode, with bath gas present, causes the ions to drift at a finite rate towards the center axis of the quadrupole assembly, and the drift caused by application of an asymmetric waveform causes a given type of ion to drift towards the rod, the balance between these forces establishes a region in which the ions drift neither to the rods nor to the center axis. A focus region is thus formed.

The application of the asymmetric waveform to quadrupole rods as discussed above leads to ion drift and loss to the electrodes unless a compensating force exists. In most FAIMS technologies previously considered however, a compensation voltage is applied to reverse this drift. In the case of quadrupole rods carrying the asymmetric waveform, simply applying a dc voltage difference between the rods as a compensation voltage seems straightforward. In fact, application of dc voltages to a set of quadrupoles operating in rf-only mode converts operation into a mass-analyzing mode of operation, and only some of the ions having appropriate mass-to-charge ratios are maintained between the rods. The combined separation by quadrupole rods operated in mass analysis and in FAIMS mode offers advantages in some situations. Clearly, this invention describes a compromise operation that combines some FAIMS separation and some mass analysis because of the dc voltages.

Several experiments can be performed using the invention described here, within the scope of the present invention. The following are non-limiting examples for illustrative purposes.

Experiment #1 is performed using an instrument mechanically identical to a triple quadrupole system where additionally the collision quadrupole is connected to electronics that permit a phase shift of the sinusoidal waves used to form the applied waveform. All conventional tandem MS experiments are performed with the collision quadrupole operated in rf-only mode with a symmetrical waveform. Experiment #1 requires filling the collision cell with gas to a pressure that is suitable for operation in FAIMS mode, and is sufficiently low pressure that conventional rf-only mode will also function, with collisional cooling. This high pressure will not necessarily correspond to pressures used in collision-induced-dissociation (CID) experiments. It is likely that performance of the rf-only mode at this pressure will also be less-than-optimum. In this experiment the user selects several parameters including the waveform voltage for operation in FAIMS mode, the phase angle for formation of the asymmetric waveform, and the dc voltage difference between rods (corresponding to the CV in conventional FAIMS) and the temperature and pressure of the cell. Experimentally, the operator finds that the collision quadrupole operating in this manner transmits a sub-set of the ions delivered to the entrance of the quadrupole rods. The selection of ions is dependent on the low-mass cutoff that is effective under the conditions of voltage and frequency and dimensions of the rods. Moreover the selection also is dependent on the degree of asymmetry of the waveform; the type, temperature and pressure of the bath gas; and the dc voltage difference between the rods and the dimensions of the space. Note also that this dc voltage difference between rods also contributes to loss of stability of some range of m/z of ions. The sub-set of ions passing through the quadrupole assembly can advantageously include one or more ions of interest, having lost other background or interfering ions via collision with the quadrupole rods. This experiment demonstrates the operation of the cell in a combined rf and FAIMS mode.

This experiment #1 is optionally performed on many instruments with varied geometry including (non-limiting examples) QqTOF, QqFTMS, as well as the QqQ described above. TOF is a time of flight mass analyzer, FTMS is a so-called fourier transform MS which is an ion cyclotron instrument. For clarity, a triple quadrupole instrument may be called qQqQ, where lower case means the quadrupole typically operates in rf-only mode, either at high or low gas pressure. The upper case means the quadrupole is a mass analyzer.

Experiment #2 is performed on an instrument with segmented quadrupole rods in the collision cell. This experiment is similar to that of Experiment #1, but the segments of the quadrupole are biased to pull the ions through the quadrupole. At the high gas pressures necessary for operation in FAIMS mode, the translational motion of the ions is retarded by the bath gas, and the transmission of ions could be very low. The longitudinal electric field is generated by biasing the segments (superimposed on rf voltages, dc voltages for FAIMS operation, and the asymmetric waveform) with voltages in a series of decreasing potentials (e.g. decreasing for positive ions, increasing for negative ions). This longitudinal field carries the ions along the length of the assembly, and they are transmitted out of the collision cell into the final analyzer (quadrupole, TOF, FTMS etc. etc.).

Experiment #3 can be performed on any of the instruments used for experiments #1 and #2. This experiment differs from the previous experiments in that the rf-only and FAIMS modes are operated sequentially in time. For a first short time the voltages applied to the quadrupoles are suitable for rf-only mode, and for a second period of time the voltages are appropriate for FAIMS operation. This experiment is optionally performed on an instrument that has a collision quadrupole that is segmented and also includes entrance and exit plates to which stopping voltages can be applied for retaining the ions in the cell for periods of time selected by the operator. Some aspects of the Experiment #3 has been described with regard to FIGS. 4a-4f. Since this mode of operation will result in a non-uniform delivery of ions out of the cell, for example a pulse of ions, the mass analyzer following this cell is most likely to be a TOF system that can do mass analysis on the transient cloud of ions extracted from the cell. While operating in this mode, the mass spectra collected will differ from spectra collected with the quadrupole assembly in conventional, low-pressure rf-only mode, or rf-mode with collisional cooling with low pressure gas, or in higher pressure CID mode. The mass spectra will be enhanced by selectivity for the ions of interest, for which operating conditions of pressure, gas composition, cell temperature, asymmetric waveform voltage and phase shifts, and dc voltages (compensation voltage and m/z selection) have been selected by the operator. Ions of other types will collide with the rods of the quadrupole assembly.

Experiment #4 is similar to the experiments described above, with the first quadrupole operated in a mass analysis mode, to provide a first selection of ions for the collision cell. The cell operated in rf-only mode, and in FAIMS mode, either in sequential (Experiment #3) or continuous superimposed mode (Experiment #1 and #2). It is an advantage of this experiment that one or more species that coexist with the same m/z as selected by the first quadrupole will then be separated and the operator obtains mass spectra that reflect the abundances of the species selected using the experimental conditions of rf-only and FAIMS modes that are available. A first condition of operation in the FAIMS mode may provide a spectrum of species A, whereas a second condition shows species B, where the original m/z of A and B were sufficiently similar (or identical) and were both therefore delivered through the first quadrupole into the collision cell that is used in these experiments for the rf-only and/or FAIMS experiments.

Experiment #5 is performed on an instrument that differs substantially from those described above. A conventional collision cell has limitations. The primary weakness of the conventional high pressure cell is that the ions from a low pressure region (including the mass analyzer directly in front of the cell) are inefficiently transmitted into a region of high gas pressure because of the outpouring of gas through the entrance orifice of the cell. This leaking flow of gas cannot be avoided in a high pressure cell that is located totally within the confines of a low pressure mass spectrometer chamber. At elevated cell pressures this transport of ions into the cell becomes more difficult and less efficient. This problem is overcome in Experiment #5, by locating this special combined rf-only and FAIMS cell directly behind the entrance orifice of the mass spectrometer. The flow of gas into the vacuum chamber carries the ions into this cell, and the efficiency of ion transport into the cell is good. In many instruments a high pressure quadrupole (often called Q0) is located between the orifice leading into the mass spectrometer and the first analyzer quadrupole. This quadrupole (or hexapole or octapole) is used to collimate the beam by collisional cooling in rf-only mode, prior to transport into the other mass analyzers.

This new high-pressure combined rf-only and FAIMS quadrupole cell can optionally be enclosed with control for pressure and gas composition, or a component of the differential pumping system, as part of the management of gas entering the vacuum chamber. This new high-pressure combined rf-only and FAIMS quadrupole cell can be operated in sequential alternation between rf-only and FAIMS mode. The cell can also be operated in a combined mode where the operator selects values for several parameters including the composition and pressure of the bath gas, the voltage and phase angle for formation of the asymmetric waveform, and the dc voltage difference between rods (corresponding to the CV in conventional FAIMS). Experimentally the operator will find that the quadrupole operating in this manner will transmit a sub-set of the ions delivered to the entrance of the quadrupole rods. The selection of ions will be dependent on the low-mass cutoff that is effective under the conditions of voltage and frequency of the waveform and dimensions of the rods. Moreover the selection will also be dependent on the degree of asymmetry of the waveform, the type and pressure of the bath gas, the dc voltage difference between the rods. Note also that this dc voltage difference between rods will also contribute to loss of stability of some range of m/z of ions. The sub-set of ions passing through the quadrupole assembly can advantageously include one or more ions of interest, but lacking other background or interfering ions that were lost via collision with the quadrupole rods.

As noted previously, application of the asymmetric waveform to quadrupole rods to achieve the FAIMS mode of operation can be applied in many ways and moreover, can be applied to one or more rods of the quadrupole assembly. Application to one quadrupole rod is not equivalent to two rods on one side or two rods at opposite sides of the assembly. For example, referring again to FIGS. 5a to 5d wherein the asymmetric waveform is applied to opposite rods, it should be pointed out that this physically symmetrical arrangement produces weak electric fields near the center axis of the quadrupole assembly in the vicinity of the ion labeled 44 in FIG. 5c, even at the times during which the voltage applied to rods 30 is at a maximum. The electric field at the center of the rod assembly is not necessarily zero if the asymmetric waveform is applied to one rod, or to two rods that are adjacent to each other. Behavior of ions in each of these cases can be readily deduced with understanding of the mechanism of FAIMS focusing and ion separation.

It is an advantage of at least some of the embodiments of the instant invention that ions are introduced into and extracted from the analyzer region between the quadrupole rods during rf-only mode of operation. Accordingly, ion transmission efficiency is enhanced relative to other electrode geometries in which the ions are introduced and extracted during FAIMS operation. In particular, ions exiting from between electrodes of a FAIMS device experience a rapid transition from balanced conditions to unbalanced conditions as a result of the abrupt disappearance of the asymmetric waveform beyond the end of the electrodes. Such ions experience only the CV that is typically applied to one of the electrodes, which causes the ion to be rapidly attracted to such an electrode. The instant invention, as described with reference to the above-mentioned embodiments, provides an elegant solution to the same problem, in which the ions are introduced and extracted during a mode of operation in which each electrode rod is maintained at a same dc potential relative to every other electrode rod. Furthermore, by collisionally cooling the ions prior to extraction, the ions are focused into a narrow beam within the analyzer region prior to being extracted. Accordingly, the above-mentioned embodiments of the instant invention are suitable for separating ions according to the FAIMS principle prior to performing other types of analysis, such as for example analysis by time-of-flight (TOF) mass spectrometry. This supports, for example, performing mobility based separations of isobaric (same m/z ratio) ions, which otherwise would be indistinguishable by mass spectral analysis. Furthermore, as was described in WO 01/69647, the FAIMS analyzer portion is effectively "electronically removed" from the system when not in use by operating the quadrupole assembly in rf-only mode.

Figure 8:
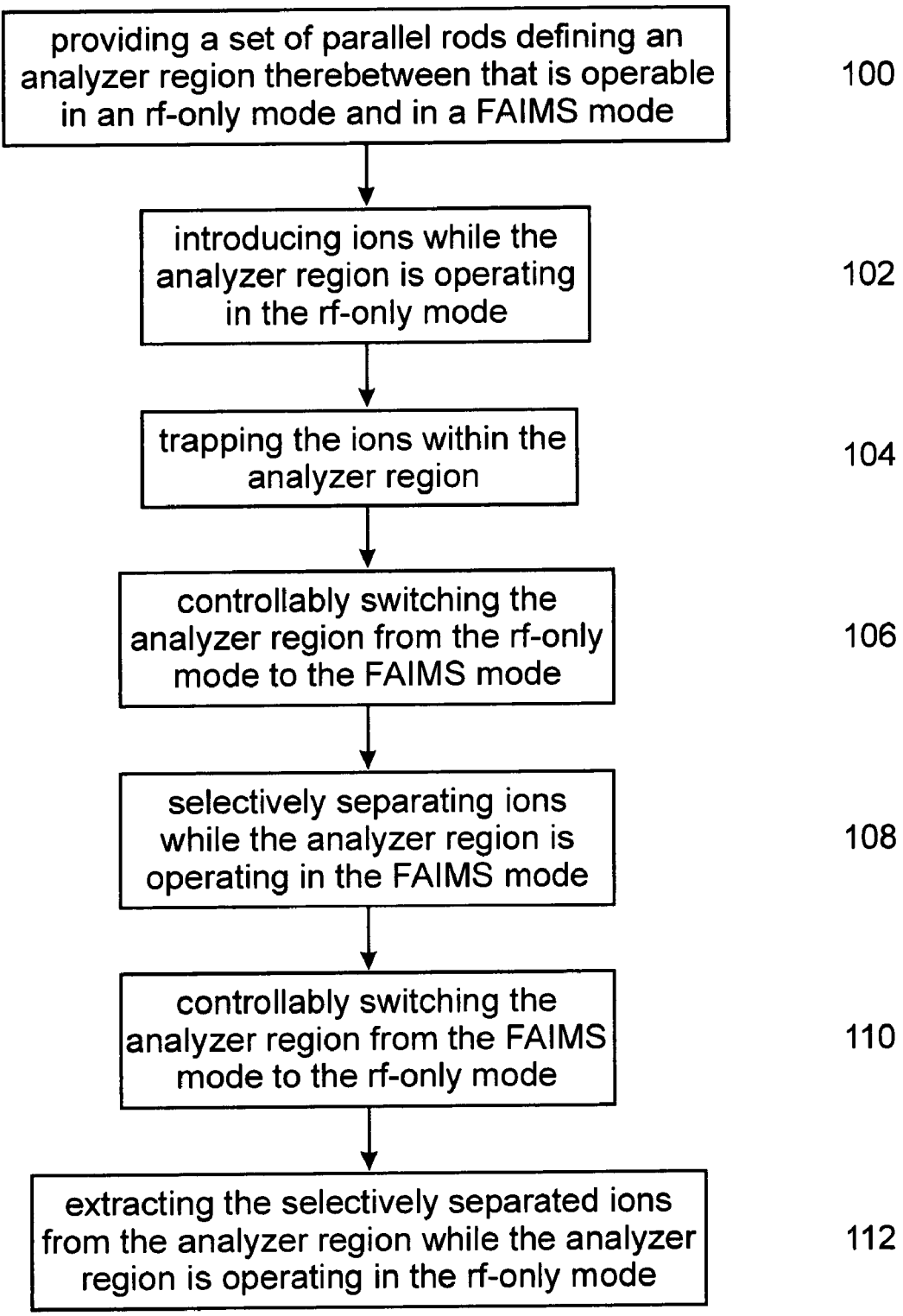
FIG. 8 shows a method of separating ions according to an embodiment of the instant invention.

Referring now to FIG. 8, shown is a method of separating ions according to an embodiment of the instant invention. At step 100, a set of parallel rods having a space therebetween is provided, the space having first and second ends and defining an analyzer region that is operable in an rf-only mode and in a FAIMS mode. For example, four parallel rods are provided. Of course, a number of parallel rods other than four optionally is provided. At step 102, ions are introduced into the analyzer region while the analyzer region is operating in the rf-only mode. At step 104, the ions are trapped within the analyzer region. For example, the ions are trapped by the application of selected electric potentials, or "stopping potentials" at the ends of the analyzer region via an ion entrance lens and an ion exit lens. Optionally, the ions are trapped by the application of different dc potentials between adjacent sets of segments of a set of parallel segmented-rods. Further optionally, the trapping is achieved, at least in part, by directing a gas flow in a direction opposite a direction of ion flow through the analyzer region. At step 106, the analyzer region is controllably switched from the rf-only mode to the FAIMS mode. For example, the symmetric rf waveform applied between the set of parallel rods is replaced by an asymmetric waveform along with a concomitant application of a compensation voltage between the set of parallel rods to maintain some of the ions along stable trajectories. At step 108, the ions are selectively separated while the analyzer region is operating in the FAIMS mode. At step 110, the analyzer region is controllably switched from the FAIMS mode to the rf-only mode. At step 112, the selectively separated ions, which remain within the analyzer region, are extracted from the analyzer region while the analyzer region is operating in the rf-only mode. For instance, the ions are subjected to an electric field by application of dc voltages to segments of a set of parallel segmented-rods, and the ions drift out through the second end.

Figure 9:
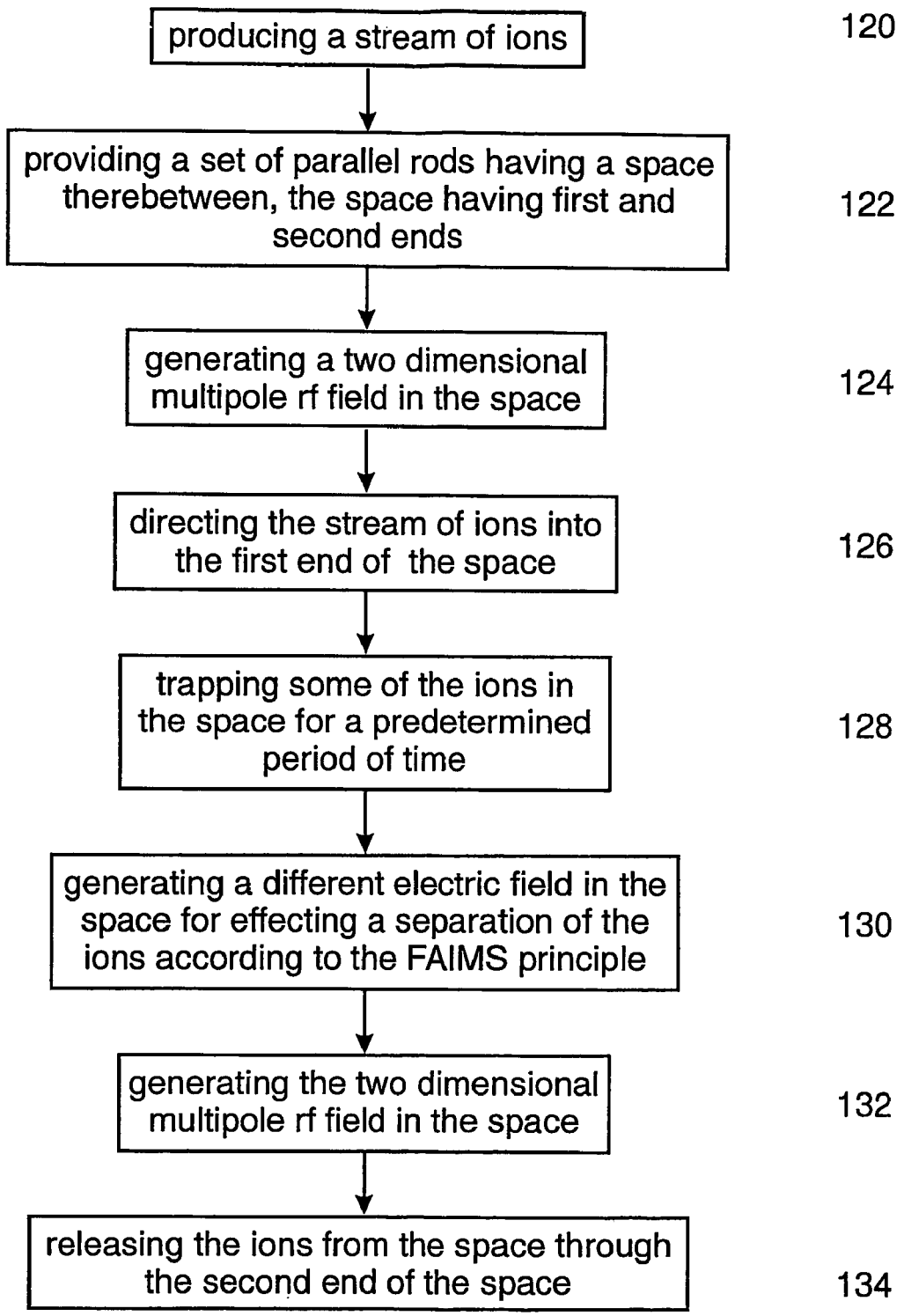
FIG. 9 shows another method of separating ions according to another embodiment of the instant invention.

Referring now to FIG. 9, shown is another method of separating ions according to another embodiment of the instant invention. At step 120 a stream of ions is produced. For instance, a stream of ions is produced at an ionization source from a suitable sample. Some non-limiting examples of suitable ionization sources include: electrospray ionization sources; corona discharge sources; radioactive ionization sources (i.e. beta-emitter); photoionization; atmospheric pressure chemical ionization source; etc. Optionally, the stream of ions is produced as a sample effluent from a different analyzer. At step 122 a set of parallel rods having a space therebetween is provided, the space having first and second ends. At step 124 a two dimensional multipole rf field is generated in the space by applying an rf voltage to the set of parallel rods. At step 126 the stream of ions is directed into the first end of the space. At step 128 some of the ions are trapped in the space for a predetermined period of time. For instance, the trapping is performed by applying selected electric potentials, or stopping voltages, at the ends of the space to cause ions traveling in the space toward the first or the second end to be diverted back toward the space between the first and second ends. Optionally, the ions are trapped by the application of different dc potentials between adjacent sets of segments of a set of parallel segmented-rods. Further optionally, the trapping is achieved, at least in part, by directing a gas flow in a direction opposite a direction of ion flow through the analyzer region. At step 130 a different electric field is generated in the space by applying an asymmetric waveform voltage and a compensation voltage to the set of parallel rods. The different electric field is for effecting a separation of the ions according to the FAIMS principle. At step 132 the two dimensional multipole rf field is generated in the space by applying the rf voltage between the parallel rods of the set of parallel rods. This returns the set of parallel rods to an rf-only mode of operation. Optionally, collisional cooling of the ions is performed so as to focus ions within the space along a central axis of the set of rods. At step 134 ions are released from the space through the second end of the space. For instance, the ions are subjected to an electric field by application of dc voltages to segments of a set of parallel segmented-rods, and the ions drift out through the second end.

Optionally, ions are introduced into the analyzer region while the analyzer region is operating in the FAIMS mode. The ions are trapped and selectively separated according to the FAIMS principle as described above. Subsequently, the analyzer region is controllably switched to the rf-only mode, and ions remaining within the analyzer region are extracted, either with or without a step of collisional cooling.

The present invention recognizes that rf-only operation of quadrupoles, and FAIMS operation of the same electrodes, can be conducted within an intermediate pressure range between the pressures where each technology may be ideally suitable. For example, the pressure range from $10^{-6}$ torr to 100 torr would encompass this region of intermediate behavior of both technologies. The selection of the pressure of operation will be dependent on the relative importance of rf-only-like or FAIMS-like performance that is required. At low pressures, for example $10^{-6}$ torr or lower, the behavior of rf-only mode will predominate, and for example application of a dc voltage difference (analogous to CV in FAIMS) between the rods may result in a reduction of the range of the m/z of ions having stable trajectories in the quadrupole assembly. On the other hand, above 100 torr, the application of the asymmetric waveform to opposite pairs of electrodes and an appropriate dc voltage as CV will result in ions approaching one pair of the electrodes, and becoming focused in a region around these rods. At this high pressure the application of only a symmetric waveform will not have useful effects and the ions will rapidly be lost to the rods.

Numerous other embodiments may be envisaged without departing from the spirit and scope of the instant invention.

What is claimed is:

1. A method of separating ions comprising the steps of:
providing an analyzer region that is operable in both an rf-only mode and in a FAIMS mode;
introducing ions into the analyzer region;
effecting a selective separation of the ions within the analyzer region substantially during operation in the FAIMS mode;
controllably switching the analyzer region from the FAIMS mode to the rf-only mode; and,
extracting the selectively separated ions from the analyzer region substantially during operation in the rf-only mode.

2. A method according to claim 1, comprising a step prior to the step of effecting a separation of the ions of: trapping some of the introduced ions within the analyzer region by the application of selected electric potentials at the ends of the analyzer region.

3. A method according to claim 1, wherein the analyzer region is provided as a space between a set of parallel rods, the space having first and second ends.

4. A method according to claim 1, wherein the ions are introduced into the analyzer region substantially during operation of the analyzer region in the rf-only mode.

5. A method according to claim 4, comprising a step prior to the step of selectively separating ions of: controllably switching the analyzer region from the rf-only mode to the FAIMS mode.

6. A method according to claim 5, comprising a step prior to the step of controllably switching the analyzer region from the rf-only mode to the FAIMS mode of: collisionally cooling the ions so as to confine the ions within a volume that is smaller than a volume occupied by the ions prior to collisional cooling.

7. A method according to claim 1, wherein the ions are introduced into the analyzer region substantially during operation of the analyzer region in the FAIMS mode.

8. A method according to claim 6, comprising a step prior to the step of extracting ions of: collisionally cooling the selectively separated ions.

9. A method according to claim 8, comprising a step prior to the step of extracting the selectively separated ions of: controllably switching the analyzer region from the rf-only mode to the FAIMS mode, so as to effect a selective second separation of the collisionally cooled selectively separated ions.

10. A method according to claim 2, wherein the step of extracting the selectively separated ions includes a step of applying a different selected electric potential at the second end of the analyzer region.

11. A method according to claim 1, comprising a step of providing the extracted selectively separated ions to one of a detector, an analyzer and an ion collector.

12. A method according to claim 6, comprising a step after the step of extracting the selectively separated ions of: refilling the analyzer region with ions while the analyzer region is operating in the rf-only mode.

13. A method according to claim 3, wherein the set of parallel rods has a quadrupole configuration.

14. A method according to claim 13, wherein each parallel rod of the set of parallel rods includes a plurality of coaxially aligned segments.

15. A method according to claim 14, wherein the selectively separated ions are extracted from the analyzer region as a result of an electric field established within the analyzer region by application of different dc voltages between different sets of segments of die parallel rods.

16. A method according to claim 1, wherein the gas pressure in the analyzer region is in the range between $10^2$ torr to $10^{-6}$ torr.

17. A method according to claim 1, wherein the gas pressure in the analyzer region is in the range between 10 torr to $10^{-4}$ torr.

18. A method according to claim 1, wherein the gas pressure in the analyzer region is in the range between 5 torr to $10^{-2}$ torr.

19. An apparatus for separating ions comprising:
a set of parallel rods having a space therebetween, the space having first and second ends and defining an analyzer region; and,
an electrical controller for electrically coupling to the set of parallel rods, for applying a radio frequency (rf)-voltage between the parallel rods of the set of parallel rods in a rf-only operating mode, for applying a combination of an asymmetric waveform voltage and a direct current voltage between the parallel rods of the set of parallel rods in a FAIMS operating mode, and for controllably switching between the rf-only operating mode and the FAIMS operating mode, wherein, during use, an ion which is being transmitted through the analyzer region is subjected to the rf-only operating mode and to the FAIMS operating mode during a period of time the ion is resident within the analyzer region.

20. An apparatus according to claim 19, comprising trapping members disposed proximate the first and second ends of the space for providing a stopping voltage, the stopping voltage for cooperating with the rf-voltage in the rf-only operating mode and for cooperating with the combination of an asymmetric waveform voltage and a direct current voltage in the FAIMS operating mode to constrain ions within the space between the first and second ends.

21. An apparatus according to claim 19, wherein the set of parallel rods has a quadrupole configuration.

22. An apparatus according to claim 19, wherein each parallel rod of the set of parallel rod comprises a plurality of coaxially aligned segments in an end-to-end arrangement.

23. An apparatus according to claim 22, comprising an electrically insulating member disposed between adjacent segments of the coaxially aligned segments within a same parallel rod.

24. An apparatus according to claim 20, wherein the trapping members comprise an ion entrance lens disposed adjacent the first end of the space and an ion exit lens disposed adjacent the second end of the space.

25. An apparatus according to claim 19, wherein the set of parallel rods includes six parallel rods.

26. An apparatus according to claim 19, wherein the set of parallel rods includes eight parallel rods.

27. An apparatus according to claim 19, comprising a housing for containing the set of parallel rods and for maintaining a predetermined atmosphere including a bath gas within the analyzer region.

28. A method according to claim 3, wherein the set of parallel rods has a hexapole configuration.

29. A method according to claim 3, wherein the set of parallel rods has an octapole configuration.

30. A method according to claim 13, wherein the step of controllably switching the analyzer region from the FAIMS mode to the rf-only mode comprises controllably changing a waveform applied to pairs of opposite rods of the parallel rods, by changing a relative phase shift of two component sinusoidal waves of the waveform.

31. A method according to claim 30, wherein the step of controllably switching the analyzer region from the FAIMS mode to the rf-only mode comprises changing the dc voltages applied to the pairs of opposite rods of the quadrupole.

32. A method according to claim 13, wherein the selective separation of the ions within the analyzer region during operation in the FAIMS mode comprises a mass analysis separation.

33. A method according to claim 14, comprising establishing a potential gradient along a length of the analyzer region for trapping at least some of the introduced ions within the analyzer region.

34. An apparatus according to claim 21, wherein, during use, an output waveform of the electrical controller is controllably changed from the rf-voltage to the asymmetric waveform voltage by changing a relative phase shift of two component sinusoidal waves of the output waveform.

35. A method according to claim 1, comprising a step prior to the step of extracting ions of: collisionally cooling the selectively separated ions during operation in the rf-only mode.

36. A method according to claim 35, comprising a step prior to the step of extracting the selectively separated ions of: controllably switching the analyzer region from the rf-only mode to the FAIMS mode, so as to effect a selective second separation of the collisionally cooled selectively separated ions.

* * * * *

UNITED STATES PATENT AND TRADEMARK OFFICE
CERTIFICATE OF CORRECTION

PATENT NO.        : 7,285,774 B2
APPLICATION NO. : 10/529304
DATED             : October 23, 2007
INVENTOR(S)       : Roger Guevremont It is certified that error appears in the above-identified patent and that said Letters Patent is hereby corrected as shown below:

Col. 20 line 64
replace "different sets of segments of die parallel rods"
with --different sets of segments of the parallel rods--

Signed and Sealed this

Second Day of December, 2008

JON W. DUDAS
*Director of the United States Patent and Trademark Office*